United States Patent [19]

De Volpi

[11] 4,092,542
[45] May 30, 1978

[54] HIGH-RESOLUTION RADIOGRAPHY BY MEANS OF A HODOSCOPE

[75] Inventor: Alexander De Volpi, Hinsdale, Ill.

[73] Assignee: The United States of America as represented by the United States Department of Energy, Washington, D.C.

[21] Appl. No.: 763,436

[22] Filed: Jan. 27, 1977

[51] Int. Cl.$^2$ .................. G01T 3/00; G01N 23/04
[52] U.S. Cl. .................. 250/392; 250/358 R
[58] Field of Search ........... 250/358 R, 363 S, 390, 250/391, 392, 505

[56] References Cited

U.S. PATENT DOCUMENTS 3,792,273   2/1974   Bergstedt ................. 250/363 S

OTHER PUBLICATIONS

De Volpi et al., "Fast-Neutron Hodoscope at Treat: Data Processing, Analysis, and Results," Nuclear Technology vol. 30, Sep. 1976, pp. 398–421.

Primary Examiner—Davis L. Willis
Assistant Examiner—Janice A. Howell
Attorney, Agent, or Firm—Dean E. Carlson; Frank H. Jackson; Donald P. Reynolds

[57] ABSTRACT

The fast neutron hodoscope, a device that produces neutron radiographs with coarse space resolution in a short time, is modified to produce neutron or gamma radiographs of relatively thick samples and with high space resolution. The modification comprises motorizing a neutron and gamma collimator to permit a controlled scanning pattern, simultaneous collection of data in a number of hodoscope channels over a period of time, and computerized image reconstruction of the data thus gathered.

6 Claims, 1 Drawing Figure

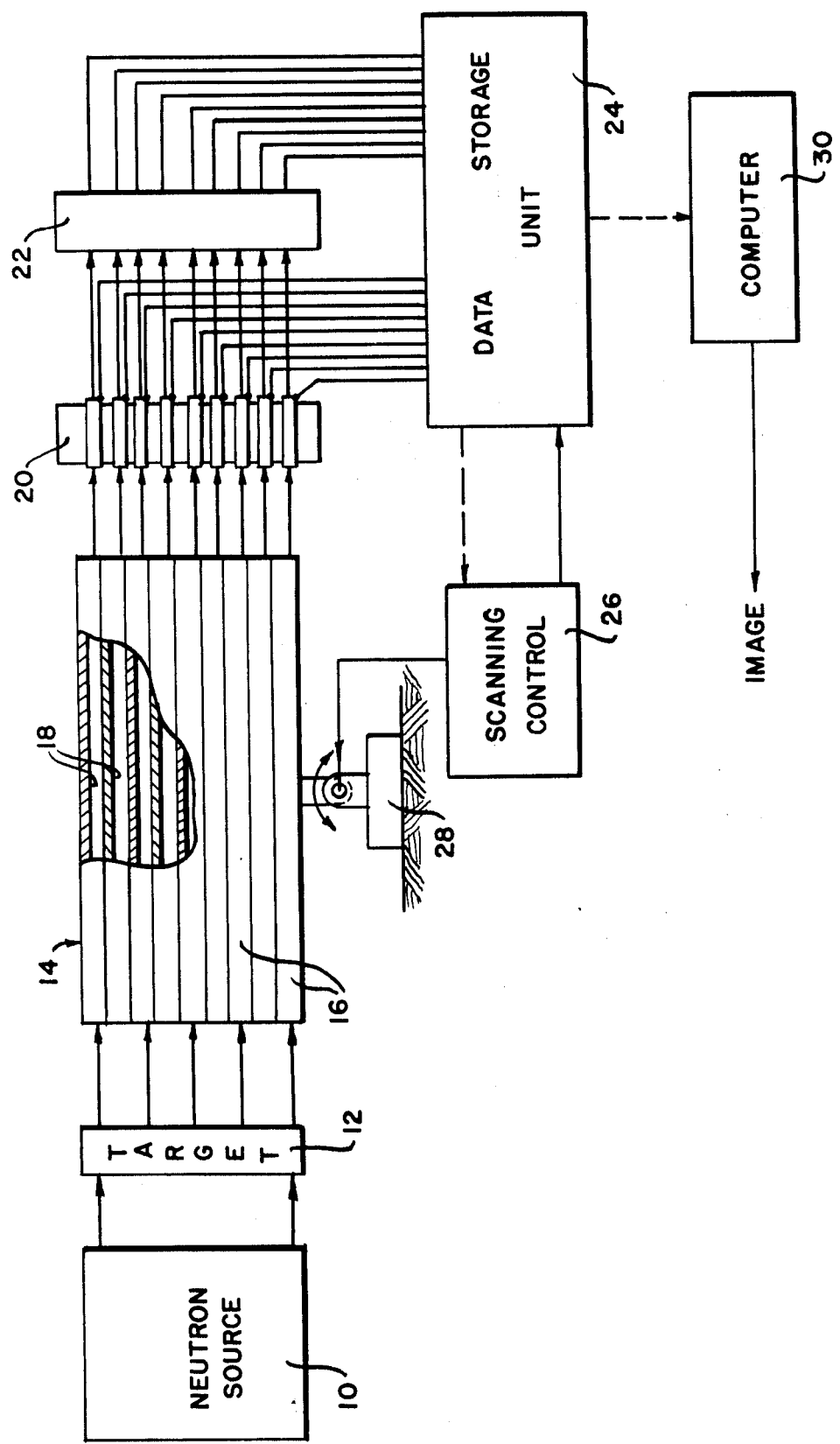

HIGH-RESOLUTION RADIOGRAPHY BY MEANS OF A HODOSCOPE

CONTRACTUAL ORIGIN OF THE INVENTION

The invention described herein was made in the course of, or under, a contract with the UNITED STATES ENERGY RESEARCH AND DEVELOPMENT ADMINISTRATION.

BACKGROUND OF THE INVENTION

This invention relates to radiography by neutrons and gamma rays.

The Transient Reactor Test (TREAT) Facility is an apparatus for performing safety tests on various phases of nuclear reactor operation. It includes a nuclear reactor to apply transient bursts of neutrons to irradiate a sample located within the reactor core. The sample typically consists of one or more fuel pins enclosed within protective test sections. It is of considerable interest to know what happens to such fuel pins and their enclosing structures upon the incidence of a sudden burst of neutrons. A hodoscope is used to determine this. In the hodoscope, a neutron collimator is placed near the test specimen to pass neutrons preferentially in straight lines toward an array of neutron detectors. Each neutron detector is aligned with a channel in the collimator and responds primarily to neutrons that have proceeded from a sample such as the fuel pins through the collimator to the neutron detector. A gamma detector is normally placed in front of or behind each neutron detector to provide additional information. For measurements involving fuel pins, it is useful to detect the fast neutrons resulting from fission of fissionable material in the fuel pins as a result of the incidence of a burst of neutrons generated by TREAT. However, operation of the hodoscope is not limited to reactor bursts. It is possible to use the hodoscope in the manner described to obtain distinctive static neutron or gamma radiographs of any test sample having properties that will affect the incident flux of neutrons by reflecting, deflecting, or absorbing portions of the neutron flux, or by generating gamma rays in response to the flux of neutrons. In the following, a radiograph is defined as an image obtained by using information from the effects of a target upon incident radiation, including that of gamma rays and neutrons. For studies of fuel pins that contain fissionable material, it is simpler to detect the fast neutrons by using neutron detectors that are responsive selectively to fast fission neutrons and respond little or not at all to neutrons characteristic of the incident flux that may enter the collimator.

The studies that have been carried out at the TREAT Facility have concentrated on observations of damage to fuel pins subjected to transient bursts. If a fuel pin is damaged by such a burst, it typically assumes a deformed shape. It is of interest to record when, where and how it is deformed. One way of doing this is to connect each of the neutron or gamma detectors to a digitizing system which is connected to an indicator such as a neon bulb. The neon bulbs are flashed periodically at frequencies of several thousand cycles per second to indicate the detection of neutrons. The patterns of lights are recorded on film in a high-speed framing camera that is synchronized with pulses of the bulbs. Alternatively, each detector can be connected to produce a record on magnetic disks or tape. The typical neutron detector has a cross-sectional area that permits the stacking of detectors in an array such that detectors are spaced approximately 38 mm apart in one direction and 22.5 mm apart in the orthogonal direction. This spatial resolution of detectors is then the spatial resolution that is obtained of the neutron time-resolved image, and of the gamma rays, when a gamma detector is disposed ahead of or behind each neutron detector. The combination of this relatively crude spatial resolution with the relatively high time resolution afforded by pictures taken as frequently as one millisecond apart provides an excellent picture of failure modes in nuclear fuel rods. There are, however, situations in which it would be useful to forgo the time resolution and to gain better spatial resolution. For example, it might be desirable to obtain a detailed measure in situ of the quality of the cladding in a fuel rod or the placement of individual fuel pins within a fuel rod to be sure that the later observations of failure of such a fuel rod are not functions of an anomalous geometry. It might be desirable to measure a failed rod in situ to eliminate any further damage upon removal of the rod for external radiography. In addition, it may be desirable to obtain a neutron or gamma radiograph of relatively high resolution of structures other than fuel rods. An example is accumulation of steel resulting from destructive tests performed on clad fuel rods.

It is an object of the present invention to adapt the hodoscope to provide high-resolution neutron and gamma radiographs.

It is a further object of this invention to perform in-situ neutron and gamma radiography with high spatial resolution.

Other objects will become apparent in the course of a detailed description of the invention.

SUMMARY OF THE INVENTION

Neutron and gamma radiographs of high spatial resolution are obtained by modifying the fast-neutron hodoscope to provide a scanning motion of a collimator, storage on magnetic tape of the detector outputs and computer reconstruction of the data thus obtained. The apparatus is adapted to detect fast neutrons, gamma rays or both and to use various combinations of the information obtained from fast neutrons and gamma rays.

BRIEF DESCRIPTION OF THE DRAWING

The drawing is a schematic representation of elements of the fast-neutron hodoscope and the modifications necessary to adapt it to practice the present invention.

DETAILED DESCRIPTION OF THE INVENTION

The drawing is a representation of the fast-neutron hodoscope as modified for the practice of the present invention. In the drawing, a neutron source 10 generates a flux of neutrons or gamma rays that is incident upon a target 12. The source 10 may be in line with or surround the target 12. Depending upon the nature of the target 12, fast neutrons, gamma rays or both will pass through the target 12 or be generated within target 12 and proceed to and through a collimator 14. Collimator 14 is typically a stack of steel plates 16 into which a plurality of grooves 18 is cut. The grooves 18 provide discrete paths with minimum attenuation for the passage of neutrons and gamma rays from the target 12 to individual neutron detectors 20 and gamma detectors 22. Grooves 18 are shown as parallel for drawing convenience, but they typically fan out to fit the dimensions of neutron detectors. Gamma rays or neutrons that enter the steel plates 16 of collimator 14 are attenuated and thus prevented from passing through to the neutron detectors 20 and gamma detectors 22. The result is that each individual neutron detector 20 and gamma detector 22 responds to neutrons or gamma rays, respectively, that leave target 12 and approach collimator 14 at an entry point determined by the end of the appropriate groove 18.

Neutron detectors 20 and gamma detectors 22 are conventional detectors that produce electrical impulses upon incidence of a neutron or gamma ray, respectively. These impulses are transmitted to a data storage unit 24. In past applications of the fast-neutron hodoscope, the data storage unit 24 has included a combination of an array of pulsed neon bulbs that is photographed by a high-speed framing camera synchronized to the pulses of the neon bulbs. In other past applications of the hodoscope, information obtained as shown by gamma detectors 22 has been displayed similarly. In the alternative, it has been useful in past applications of the hodoscope to store information in a data storage unit 24 that comprises magnetic tape or magnetic disk storage. All of these applications have involved use of the hodoscope to the situation in which target 12 is a fuel rod for a nuclear reactor and when neutron source 10 produces a transient burst of neutrons so that relative motion is achieved between target 12 and collimator 14 by the deformation of the target 12 in response to the transient burst of neutrons.

The present invention is adapted to accomplish high-resolution radiography over a relatively long period of time by the following modifications to the existing hodoscope that was described above. First, a scanning control 26 is connected to the movable mount 28 of collimator 14 to permit collimator 14 to be scanned past target 12 in a predetermined pattern. The scanning may be performed manually or mechanically, either by local or remote control. Information about the predetermined pattern is coupled to data storage unit 24 which, for the purpose of high-resolution radiography, is preferably a means of data storage on magnetic tape or magnetic disks. Data from data storage unit 24 are transmitted to computer 30 for conventional image reconstruction and the reconstructed image is the high-resolution radiograph.

When the main concern in use of the hodoscope was the measurement of targets 12 that were fuel rods for nuclear reactors, then the most convenient scheme for discriminating between background neutrons and those neutrons associated with a desired image was to activate fissionable material in target 12 and detect selectively the fast neutrons resulting from that fission. The geometry of the collimator and target also reduces the effects of background neutrons. This provided useful information about the location of such fissionable material in target 12 and the response of that material to a burst of neutrons from neutron source 10. It has already proved useful in the present application of the fast neutron hodoscope to add a gamma detector 22 to correspond to each neutron detector 20 to provide additional information about target 12. This additional information is the location of gamma rays that are characteristic of particular materials that are bombarded by neutrons from neutron source 10. Using such detectors it is possible to gain information from the hodoscope in the absence of fissionable material in target 12 and it is possible to gain additional information about the location and response of nonfissionable material when target 12 is a fuel rod that includes both fissionable and nonfissionable materials. Both these types of information are useful in making a high-resolution radiograph in which neutron source 10 is so operated as not to cause physical damage to target 12. If target 12 contains fissionable material, then the neutron detectors will respond to fast neutrons produced as a result of fissions induced by neutron bombardment. At the same time gamma detectors 22 will respond to gamma rays produced by the incidence of neutrons from neutron source 10 on nonfissionable materials in target 12. The combination of these items of information with the positional information obtainable from scanning control 26 enables the development of data that permits reconstruction from computer 30 of an image that has finer spatial resolution than the spatial resolution of the array formed by the neutron detectors 20 and the gamma detectors 22.

The embodiments of the invention in which an exclusive property or privilege is claimed are defined as follows:

1. In a hodoscope for forming an image of a target irradiated by neutrons from a source to produce fast neutrons and gamma rays, the hodoscope including a collimator with channels to produce a plurality of discrete beams of fast neutrons and gamma rays, a detector of gamma rays and a detector of fast neutrons at each channel generating signals responsive to the beams, and means for reconstructing an image from the signals from the gamma and fast-neutron detectors, the improvement comprising:
   means for scanning the collimator with respect to the target;
   control means connected to the scanning means and to the means for reconstructing an image to associate the image with position of the collimator.

2. The apparatus of claim 1 wherein the means for scanning the collimator comprise a motorized mount.

3. A method of obtaining high-resolution radiographs of a target with a neutron hodoscope producing radiographs of the target comprising the steps of:
   scanning the neutron hodoscope past the target;
   associating a known position of the neutron hodoscope with radiographs produced by the neutron hodoscope;
   combining information about position with the radiographs to produce a high-resolution radiograph.

4. The method of claim 3 wherein the neutron hodoscope is a fast-neutron hodoscope.

5. The method of claim 3 wherein the neutron hodoscope is a neutron and gamma hodoscope.

6. The method of claim 3 wherein the neutron hodoscope is a fast-neutron and gamma hodoscope.

* * * * *